US009365884B2

(12) United States Patent
Nishikawa et al.

(10) Patent No.: US 9,365,884 B2
(45) Date of Patent: Jun. 14, 2016

(54) ENVIRONMENTAL EVALUATION INSTALLATION AND ENVIRONMENTAL EVALUATION METHOD

(75) Inventors: Kazuo Nishikawa, Higashiosaka (JP); Norihiro Matsuoka, Nara (JP); Tetsuya Yoneda, Yamatotakada (JP); Hisaharu Yagi, Kizugawa (JP); Masashi Kawai, Aichi (JP)

(73) Assignee: SHARP KABUSHIKI KAISHA, Osaka-Shi (JP)

( * ) Notice: Subject to any disclaimer, the term of this patent is extended or adjusted under 35 U.S.C. 154(b) by 1652 days.

(21) Appl. No.: 12/374,241

(22) PCT Filed: Jun. 27, 2007

(86) PCT No.: PCT/JP2007/062937
§ 371 (c)(1),
(2), (4) Date: Jul. 20, 2009

(87) PCT Pub. No.: WO2008/010394
PCT Pub. Date: Jan. 24, 2008

(65) Prior Publication Data
US 2009/0311741 A1 Dec. 17, 2009

(30) Foreign Application Priority Data

Jul. 20, 2006 (JP) .............................. 2006-198230
Jul. 20, 2006 (JP) .............................. 2006-198231

(51) Int. Cl.
C12Q 1/04 (2006.01)
C12Q 1/06 (2006.01)
G01N 1/22 (2006.01)
G01N 15/00 (2006.01)

(52) U.S. Cl.
CPC .............. *C12Q 1/06* (2013.01); *G01N 1/2202* (2013.01); *G01N 2015/0088* (2013.01)

(58) Field of Classification Search
CPC ....................................................... C12Q 1/06
USPC ............................................................ 435/34
See application file for complete search history.

(56) References Cited

U.S. PATENT DOCUMENTS

2005/0013729 A1* 1/2005 Brown-Skrobot et al. ..... 422/24
2005/0136508 A1 6/2005 Ponce
2007/0092928 A1 4/2007 Nishikawa

FOREIGN PATENT DOCUMENTS

| JP | 03-039081 | 2/1991 |
|----|-----------|--------|
| JP | 07-256141 | 10/1995 |
| JP | 2003-010653 | 1/2003 |
| JP | 2004-159508 | 6/2004 |
| WO | WO 00/32990 | 6/2000 |
| WO | WO 2004/067197 A1 | 8/2004 |

OTHER PUBLICATIONS

Gould et al., Activaiton of Spores of Bacillus cereus by gamma-radiation, Journal of General Microbiology, 1968, vol. 50, p. 77-84.*
Blatchely et al., Inactivaiton of Bacillus Spres by Ultraviolet or gamma radiation, Journal of environmental engineering, 2005, vol. 131, p. 1245-1252.*
Translation of JP2004/159508.*
Xu et al., Efficacy of ultraviolet germicidal irradiation of upper-room air in inactivating airborne bacterial spores and mycobacteria in full-scale studies, Atmospheric Environment vol. 37, 2003, p. 405-419.*
Miller et al., Evaluation of a Methodology for Quantifying the effect of room air ultraviolet germicidal irradiation on airborne bacteria, Aerosol Science and Technolgy, vol. 33, 2000, vol. 33 , p. 274-295.*
Kazuo Nishikawa, Air Purification Technology by Means of Cluster Ions Generated by Discharge Plasma, Appliance Systems Product Development Center, Sharp Corporation, NES 2003, The 13th Microelectronics Symposium, Oct. 2003, pp. 1-8.
S.J. Foster and K. Johnstone, Pulling the Trigger: The Mechanism of Bacterial Spore Germination, Molecular Microbiology, 1990 4(1), 137-141.

* cited by examiner

*Primary Examiner* — Taeyoon Kim
*Assistant Examiner* — Tiffany Gough
(74) *Attorney, Agent, or Firm* — Birch, Stewart, Kolasch & Birch, LLP

(57) ABSTRACT

An environmental evaluation installation including an evaluation chamber 1 isolated from outer space by isolation walls 2, minute substance supply means 3 configured to supply a microorganism into the evaluation chamber 1, a minute substance removing means 4 configured to supply removal particles for removing the microorganism into the evaluation chamber 1, and a minute substance collecting means 5 configured to collect the microorganism in the evaluation chamber 1, and which is characterized in that many air supply holes 21 are provided for almost the whole surfaces of the isolation walls 2 except at least the floor surface of the isolation walls 2 and that air is made to flow into the evaluation chamber 1 from the air supply holes 21.

3 Claims, 11 Drawing Sheets (a)  (b)

ENVIRONMENTAL EVALUATION INSTALLATION AND ENVIRONMENTAL EVALUATION METHOD

TECHNICAL FIELD

The present invention relates to an environmental evaluation installation and an environmental evaluation method for evaluating a minute substance in space.

BACKGROUND ART

In recent years, there has been increasing interest in improving the air environment because of the air pollution problem, the generation of various pathogenic bacteria and viruses, the increase in the number of allergy patients, and the like. In order to respond to the demand for making the indoor environment comfortable, there have been proposed removing techniques and evaluation methods of minute substances which exist in the atmosphere and which include, for example, microorganisms such as bacteria, fungi and viruses, and minute substances such as harmful chemical substances.

Conventionally, as a method for improving the air environment, there have been generally adopted various methods for removal particles in the air by using a filter. The method is configured to clean the air by physically collecting and removing the minute substances in the air.

Further, various air cleaning techniques as represented by those using radicals and ions have been attracting attention in recent years. The techniques are based on a method for eliminating the harmfulness of the minute substances floating in the air by using the effects of denaturation, decomposition, and the like. For example, as methods for performing sterilizing treatment by irradiating microorganisms with particles such as ionized ions, there has been disclosed in Patent Document 1 a positive and negative ion generation technique for cleaning the air and a sterilization method for sterilizing bacteria floating in the atmosphere by applying the technique.

In the development of a household electric appliance using such technique, a technique to measure the air environment is very important in the product development, because the design of the product, in which design the required air cleaning function, the reduction in energy consumption, and the like, are made compatible with each other, can be effected by accurately evaluating the performance of the product.

For example, as a method for detecting and quantifying how much harmful substance exist in the environment, there is disclosed in Patent Document 2 a technique relating to an apparatus and system for measuring minute substances floating in the atmosphere.

Further, it is proposed in Patent Document 3 that a quantitative evaluation of a removal effect test, which is performed by applying some actions to substances floating in a closed space, can be effectively performed by utilizing a method and apparatus for evaluating the removal of microorganisms.

Patent Document 1: Japanese Patent Laid-Open No. 2002-095731
Patent Document 2: Japanese Patent Laid-Open No. 11-14511
Patent Document 3: Japanese Patent Laid-Open No. 2004-159508

DISCLOSURE OF THE INVENTION

Problems to be Solved by the Invention

However, the technique described in Patent Document 1 represents a sterilization method by using particles such as ionized ions, but a method for effectively testing the change in quantity of minute substances is not specifically described in Patent Document 1.

Further, the evaluation apparatus described in Patent Document 2 is featured in that minute substances floating in space are collected and detected. However, the action between the floating substances and the wall surface of the evaluation chamber is not taken into account in the evaluation apparatus. When the floating substances adhere to the wall surface, it is not possible to perform accurate evaluation. Further, the kinds of minute substances capable of stably floating in the space are not taken into account.

Further, the technique described in Patent Document 3 is to evaluate the removal of floating substances. However, in the technique, the action between the floating substances and the wall surface of the evaluation chamber is not taken into account, and the kinds of microorganisms capable of stably floating in the space are not also taken into account. Thus, there is required an evaluation apparatus capable of performing further accurate evaluation.

Therefore, in view of the above, an object of the present invention is to provide an environmental evaluation installation capable of highly precisely evaluating the removal of minute substances floating in space.

Means for Solving the Problems

In order to achieve the above described object, the present invention is characterized by being configured such that minute substances are made to stably float in an evaluation chamber. Specifically, an environmental evaluation installation, according to the present invention, includes an evaluation chamber isolated from outer space by isolation walls, a minute substance supply means configured to supply a minute substance into the evaluation chamber, and a minute substance collecting means configured to collect the minute substance in the evaluation chamber, and is used to measure and evaluate the minute substance collected by the minute substance collecting means. The environmental evaluation installation is characterized in that many air supply holes are provided for almost the whole surfaces of the isolation walls except at least the floor surface of the isolation walls and that air is made to flow into the evaluation chamber from the air supply holes.

The environmental evaluation installation is capable of evaluating a time-sequential change in the concentration, and the like, of the minute substance supplied into the evaluation chamber. When the evaluation is performed, the air is made to flow into the evaluation chamber from the many air supply holes provided for almost the whole surfaces of the isolation walls. Since the minute substance near the isolation wall is repelled to the inside of the evaluation chamber by the air flow, it is possible to prevent the minute substance from adhering to the isolation wall and possible to make the minute substance stably float in the evaluation chamber. Therefore, since the minute substance can be evaluated in the state of a substantially infinite space without the influence of the wall effect, it is possible to perform more accurate evaluation.

Further, in addition to the above described configuration, it is possible to provide minute substance removing means configured to supply removal particles for removing the minute substance into the evaluation chamber. According to the apparatus, since the minute substance is collected and measured after the removal particles are irradiated in the inside space of the evaluation chamber, it is possible to evaluate the removable ability for the minute substance by irradiating the removal particles, and possible to quantitatively evaluate various conditions under which the removal particle are irradiated.

Specifically, the minute substance is time-sequentially collected by the minute substance collecting means, and the time-sequential change of the collected minute substance is measured. Thus, it is possible to evaluate the ability of the removal particles by comparing the time-sequential change of the minute substance in the case where the removal particles are not supplied by the minute substance removing means, with the time-sequential change of the minute substance in the case where the removal particles are supplied by the minute substance removing means.

It is preferred that the evaluation chamber is configured to be in a closed state except the air supply holes. Thereby, it is possible to prevent the leakage of the minute substance. Further, it is preferred that the air supply holes are formed on almost the whole surfaces of the isolation walls of the evaluation chamber except at least the floor surface, and it is more preferred that the air supply holes are formed on the whole surfaces of the isolation walls including the floor surface. When the air supply holes are formed on almost the whole surfaces, the whole inner surfaces of the evaluation chamber can be covered with the air flowing into the evaluation chamber from the holes, and thereby the adhesion of the minute substance can be effectively prevented.

Further, the isolation wall may be configured to have one layer structure. However, the isolation wall can be configured to have at least an inner wall, an outer wall, and an air flow passage formed between the inner wall and the outer wall, and configured such that many air supply holes are formed in the inner wall. By the outer wall, it is possible to prevent the minute substance from being leaked and possible to prevent minute substances, and the like, from entering from the outer space. Also, it is possible to make the air flow into the evaluation chamber from the air supply holes of the inner wall.

The air supply holes are preferably configured such that the air is radiated in the direction so as to be diffused at the time when the air is made to flow into the evaluation chamber. Thus, it is possible to form the air flow directed to the inside of the evaluation chamber over the whole inner surfaces of the evaluation chamber. As a specific configuration example of the air supply hole, there can be listed a pore having a diameter of 0.1 to 2 cm. This configuration utilizes the nature of the air that the air is, after passing through a pore, radiated in the direction to be diffused. Alternatively, the pore may be formed so that the cross-sectional area thereof is increased toward the inside of the evaluation chamber. The air is radiated in the direction to be diffused along the inclination of the wall surface forming the air supply hole. Note that the shape of the air supply hole is not limited to the circular shape, and may be formed into a polygonal shape, such as a rectangle. Further, the direction of the air supply hole need not be vertical to the wall surface, and may be inclined with respect to the wall surface.

Further, the distance W between the adjacent air supply holes is preferably set to a distance about one to three times the diameter of the hole. The air supply holes are formed over almost the whole surfaces of the isolation walls, and thereby the air flows directed to the inside of the evaluation chamber are formed over the whole inner surfaces of the isolation walls.

It is possible to provide an air intake opening for taking the air into the evaluation chamber from the outer space. The air from the air intake opening is made to flow into the evaluation chamber through the air supply holes.

Further, it is preferred that the air delivered into the evaluation chamber from the air supply holes is purified beforehand. Thus, a filter can be provided in the air intake opening. Thereby, minute substances in the outside air can be prevented from being mixed in the air delivered into the evaluation chamber.

Further, it is preferred that the temperature and/or humidity of the air delivered into the evaluation chamber from the air supply holes is adjusted. Thereby, a minute substance, particularly a microorganism, which is sensitive to the humidity and the change in the humidity, can be made to stably float in the space of the evaluation chamber. Thus, specifically, an air conditioning section configured to adjust the temperature and/or humidity can be provided on the upstream side from the air intake opening or in the air flow passage. Further, it may also be configured such that the air conditioning section is provided in the evaluation chamber. Thereby, it is possible to adjust the temperature and/or humidity in the evaluation chamber.

It is possible to provide an air exhaust opening configured to exhaust the air in the evaluation chamber to the outer space. The air delivered into the evaluation chamber from the air supply holes can be exhausted from the air exhaust opening.

It is possible to provide at the air exhaust opening an in-exhaust minute substance collecting means configured to collect the minute substance in the exhausted air. Thereby, it is possible to prevent the minute substance in the evaluation chamber from being leaked to the outside air. Further, when an impinger is used as the in-exhaust minute substance collecting means, the amount of the minute substance can be measured. Note that other means, such as a filter, may be also used other than the impinger.

Further, when the air is supplied into the evaluation chamber from the air supply holes, the inside of the evaluation chamber is brought into a pressurized state, and hence the air containing the minute substance may be leaked from the evaluation chamber to the outside of the evaluation chamber. The evaluation chamber is preferably set at the normal pressure, but is more preferably set in a negative pressure state.

As means for preventing the evaluation chamber from being brought into a pressurized state, there can be listed a method in which a movable wall configured to partition the inside of the evaluation chamber and configured to be movable in the evaluation chamber is provided, and in which the volume of the evaluation chamber can be changed by the movement of the movable wall. It is possible to prevent the evaluation chamber from being brought into a pressurized state by increasing the volume of the evaluation chamber. Note that many air supply holes are also preferably provided in the movable wall. Thereby, it is possible to prevent minute substances from adhering to the movable wall.

Further, as another means for preventing the evaluation chamber from being brought into a pressurized state, there can be listed a method of providing a suction means configured to suck the air in the evaluation chamber from the air exhaust opening, so as to thereby maintain the inside of the evaluation chamber in the negative pressure state. It is possible to lower the air pressure in the evaluation chamber by forcibly exhausting the air in the evaluation chamber to the outer space.

Note that conventionally, there exists an apparatus which is configured to control the exhaust amount so that the pressure in the evaluation chamber is kept constant. However, a variation is caused in the exhaust amount by using the apparatus. Here, the exhaust amount is regarded as an important factor in the evaluation test of the minute substance. This is because as the exhaust amount of the air from the evaluation chamber is increased, the amount of the minute substance discharged together with the air is also increased. Further, the present inventors have found that a slight pressure difference exerts almost no influence on the minute substance, such as a microorganism.

Thus, the amount of the air exhausted from the air exhaust opening may be grasped. For example, also in the case where after the exhaust amount at the time when the removal particles are not supplied is grasped, the removal particles are supplied by the minute substance removing means, the performance of the minute substance removing means can be accurately evaluated by performing the evaluation test under the same exhaust amount condition.

Specifically, it is possible to provide an exhaust amount measuring section which is configured to measure the amount of air exhausted from the air exhaust opening, and possible to provide a control section which is configured to perform an arithmetic operation on the exhaust amount from the exhaust amount measuring section and which is configured to control the suction means so as to reproduce the exhaust amount. For example, the control section performs control such that the time-sequential change in the exhaust amount in the case where the minute substance is not removed is equal to the time-sequential change in the exhaust amount in the case where the minute substance is removed. Thereby, both the evaluation tests are performed under the same condition.

Alternatively, on the basis of an exhaust amount signal from the exhaust amount measuring section, the control section is able to control the suction means so that the exhaust amount become substantially fixed. When the exhaust amount is fixed, the evaluation can be performed under the same condition at any time.

Further, it is possible that there is provided an inflow amount measuring section configured to measure the amount of air flowing into the evaluation chamber from the air intake opening, and that the control section determines whether or not the air flow in the evaluation chamber is normal, on the basis of the difference between the exhaust amount from the exhaust amount measuring section and the inflow amount from the inflow amount measuring section. For example, as the case where the air flow is abnormal, there can be listed a case where the difference between the exhaust amount and the inflow amount is larger than a predetermined value. That is, when the exhaust amount is smaller than the inflow amount, it is estimated that a leakage from the evaluation chamber is caused.

Further, it is possible to issue a warning by a notifying means at the time when the result of the above described determination is abnormal. As the notifying means, there can be listed a display in a display section such as a monitor, and notification by sound and light.

Note that a flowmeter can be used as the exhaust amount measuring section and the inflow amount measuring section, but the present invention is not limited to this.

It is possible to configure such that a taking in and out mechanism for taking the minute substance collecting means in and out of the evaluation chamber is provided, and that the taking in and out mechanism is fixed to the isolation wall and includes a container-like pass box one side of which is openable in the evaluation chamber and the other side of which is openable in the outer space, and a moving means capable of moving the minute substance collecting means between a predetermined position in the pass box and a predetermined position in the evaluation chamber.

In order to investigate the time-sequential change of the minute substance, it is necessary to exchange the minute substance collecting means. However, when the mechanism is used, a person need not go in and out of the evaluation chamber in order to exchange the minute substance collecting means. Therefore, it is possible to prevent the influence of the minute substance in the evaluation chamber on the human body, and possible to prevent the minute substances from entering the evaluation chamber from the outside. Thus, it is possible to perform more highly precise evaluation.

A door configured to be closed in an openable and closable manner can be provided at each of both end openings of the pass box. The coming and going of the minute substance between the inside and outside of the evaluation chamber can be reduced by the double door.

The moving means can be configured as a movable body which is able to travel on the floor of the evaluation chamber and to hold the minute substance collecting means. The minute substance collecting means can be moved to a predetermined position in such a manner that the movable body which holds the minute substance collecting means by a method, such as mounting, moves by traveling on the floor surface.

Alternatively, the moving means may also be configured by a guide passage provided between the pass box and the predetermined position in the evaluation chamber, and a movable body configured to hold the minute substance collecting means and to move along the guide passage.

The movable body can be provided with wheels. Thereby, the movable body can be smoothly moved. Further, the movable body can be a self-traveling type. Further, the movable body can be a form having a receiving section so as to be able to be remotely operated. The movable body can be moved to the predetermined position by remote control.

The guide passage may be installed on the floor surface of the evaluation chamber, or may also be installed on the ceiling surface of the evaluation chamber. The installation place of the guide passage is not limited to in particular.

Further, as the guide passage, there can be listed a rail, a conveyor belt, and the like, but the guide passage is not limited to these.

Further, the movable body may be configured to be hung from the ceiling surface of the evaluation chamber, and configured to be able to be moved along the guide passage installed on the ceiling surface. According to this configuration, since the guide passage is installed on the ceiling surface, the air flow in the evaluation chamber is comparatively unlikely to be disturbed.

Note that there can be listed an air sampler as the minute substance collecting means, but the minute substance collecting means is not limited to this. It is also possible to collect the minute substance by using an impinger. However, since the efficiency of the impinger in collecting floating bacteria is lower than that of the air sampler, it is preferred to use the impinger as auxiliary means of the air sampler.

Further, according to the present invention, there is provided an environmental evaluation method in which after microorganisms are supplied in an evaluation chamber isolated by isolation walls from outer space, the microorganisms are collected and the collected microorganisms are measured, the method being characterized in that spore-forming bacteria in a sporulated state are used as the microorganism in order to prevent the spontaneous disappearance of the microorganism. As a result of the investigation of the present inventors, it was found that the general activity state (nutritional state) of spore-forming bacteria and the number of floating live bacteria as the other microorganism, such as *Escherichia coli*, are greatly changed by the influences of humidity.

Thus, the spore-forming bacteria are subjected to a special treatment so as to be brought into a sporulated state. Thereby, it is possible that when the bacteria are sprayed in the air, the number of floating live bacteria is unlikely to be influenced by the humidity and that the bacteria are made to float in living state for a long time in a wide range of humidity. Therefore, since the influence due to the spontaneous disappearance (decrease) of the microorganism can be reduced, it is possible to perform more highly precise evaluation.

Further, in an environmental evaluation method in which after microorganisms and then removal particles for removing the microorganisms are supplied in an evaluation chamber isolated by isolation walls from outer space, the microorganisms are collected and the collected microorganisms are measured, the method can be configured such that spore-forming bacteria in a sporulated state are used as the microorganisms in order to prevent the spontaneous disappearance of the microorganisms. According to this method, since the microorganisms are collected to be measured after the removal particles are irradiated in the inner space of the evaluation chamber, it is possible to evaluate the effectiveness of removing the microorganisms by irradiating the removal particles, and possible to quantitatively evaluate various conditions under which the removal particles are irradiated.

Note that the spore-forming bacteria are not limited in particular, but *Bacillus subtilis* is preferred as the spore-forming bacteria. *Bacillus subtilis* is featured in that it has less adverse effect on the human body and hence can be tested safely. For this reason, for example, even when an airborne bacteria removing test by an air cleaner is performed in a large indoor space of six-mat room or more, the test person is able to safely perform the test without any danger of being exposed to the microorganism. Further, since *Bacillus subtilis* is unlikely to be influenced by humidity, it is possible to easily perform a test excellent in reproducibility without the humidity control being performed.

Further, there is a method of controlling the humidity in the evaluation chamber as another means for preventing the spontaneous disappearance of the microorganism. Specifically, the method is an environmental evaluation method in which after microorganisms are supplied in an evaluation chamber isolated from outer space by isolation walls, the microorganisms are collected and the collected microorganisms are measured, and which is characterized in that the humidity in the evaluation chamber is controlled in order to prevent the spontaneous disappearance of the microorganisms. The amount of microorganisms in the air is liable to be influenced by the humidity. Thus, it is possible to make the microorganisms float in the air in living state for a long time in such a manner that the humidity is controlled so as to be suitable for the microorganisms. Therefore, since the influence by the spontaneous disappearance (decrease) of the microorganisms can be reduced, it is possible to perform more highly precise evaluation.

Further, in an environmental evaluation method in which after microorganisms and then removal particles for removing the microorganisms are supplied in an evaluation chamber isolated from outer space by isolation walls, the microorganisms are collected and the collected microorganisms are measured, the method can be configured such that the humidity in the evaluation chamber is controlled in order to prevent the spontaneous disappearance of the microorganisms. According to this method, since the microorganisms are collected to be measured after the removal particles are irradiated in the inner space of the evaluation chamber, it is possible to evaluate the effectiveness of removing the microorganisms by irradiating the removal particles, and possible to quantitatively evaluate various conditions under which the removal particles are irradiated.

The microorganism used under the humidity control is not limited to in particular, but *Escherichia coli* can be used. *Escherichia coli* has less adverse effect on the human body, and hence is suitable as a microorganism used for evaluating the change in the number of floating bacteria. However, since the variation at the time of the test is large, there is a problem in securing the reproducibility. As a result of an extensive investigation, the present inventors have found that the number of live bacteria is greatly changed by the influence of the humidity in the test environment. As for *Escherichia coli*, in the environment in which the humidity is low, the number of floating live bacteria is quickly reduced. Thus, for example, when the performance of an air cleaner in removing floating bacteria is investigated, there has been a problem that the airborne time of the bacteria for evaluating the removing performance cannot be secured. However, the airborne time can be increased by performing control to increase the humidity. Thereby, it is possible to obtain the advantage that the time for investigating the removing performance can be increased. Further, it is possible to perform a test with less variation and excellent in reproducibility by controlling the humidity.

Further, the relative humidity in the test atmosphere is preferably set to 45% or more. FIG. 8 shows the results of investigation about the correlation between the relative humidity and the floating amount of *Escherichia coli*, which investigation was performed by the present inventors, and shows the results obtained by investigating the number of floating live bacteria at 0 to 60 minutes after the change of the humidity. As can be seen from the figure, it is possible to hold a large floating amount of *Escherichia coli* by setting the relative humidity to 45% or more.

The humidity in the test atmosphere can be adjusted by using an ultrasonic humidifier. As the humidifier, there are generally a type based on a method of evaporating water by heating, a type based on a method of dispersing water in the air by ultrasonically providing energy to the water, and a type configured by combining both the methods. According to the investigation performed by the present inventors, it was found that among these methods, the method of heating water has a drawback that the floating time of bacteria cannot be kept long.

It is estimated that in the method of heating water, high temperature water vapor has a function of sterilizing microorganisms in the air and thereby the decrease in the amount of microorganisms is accelerated. On the other hand, the ultrasonic humidifying method, in which the decrease in the amount of floating bacteria is slow, is hence suitable for the floating test of microorganisms. It is estimated that since high temperature water vapor is not generated in the ultrasonic humidifying method, the floating state of microorganisms can be maintained in the state where the microorganisms are hardly sterilized.

Note that as the minute substance in the present invention, there are listed microorganisms in the concept including bacteria, fungi (including mold), viruses, allergen substances (including ticks), and the like, house dust, powder dust, pollen, odor, harmful chemical substance, and the like, but the minute substance is not limited to these. Further, the microorganism is not limited to those having an adverse effect on the human body, and includes those having a favorable effect on the human body. The aroma is also included in the odor.

Further, as the minute substance to be removed, it is possible to use one type or a combination of two or more types which are selected from the above described group. Also, as the microorganism, it is possible to use one type or a combination of two or more types which are selected from the group including bacteria, fungi, viruses, and allergen substances.

Thereby, it is possible to use various minute substances as the object of the removal evaluation according to the present invention.

Note that spore-forming bacteria in a sporulated state are preferably used as the microorganism and *Bacillus subtilis* is preferably used as the spore-forming bacteria. Further, when the spore-forming bacteria in a sporulated state are not used as the microorganism, it is preferred that the relative humidity in the environment of the evaluation chamber is set to 45% or more.

The minute substance can be supplied to the inner space of the evaluation chamber in such a manner that a solution in which the minute substance is dispersed is sprayed in the form of mist. Thereby, it is possible to easily supply the minute substance into the evaluation chamber, and possible to easily perform the removing treatment of the minute substance. Then, in the case where such minute substance is sprayed in the form of mist, the minute substance can be used as the evaluation object according to the present invention.

Further, the minute substance can be supplied to the inner space of the evaluation chamber in such a manner that the inner space of the evaluation chamber is stirred from below the minute substance supplied into the evaluation chamber. Thereby, when the minute substance is supplied into the evaluation chamber, it is possible to prevent the natural sedimentation of the minute substance by its own weight and possible to effectively perform the removing treatment by irradiating the removal particles.

Further, as the removal particles for removing the minute substance, it is possible to use a gas generated by one of electric discharge in the air, irradiation of emitted light in the air, and the Lenard effect. Further, as the removal particles, it is possible to use emitted light, X-ray, gamma ray, or electromagnetic waves. Further, as the removal particles, it is possible to use positive and/or negative ions.

Here, in the following, there will be described a reason why when positive and negative ions are used as the specific removal particles for sterilizing a minute substance, particularly a microorganism, the sterilizing treatment of the microorganism can be performed.

That is, when positive and negative ions are generated by ionization phenomena, such as electric discharge, caused in the atmosphere, there are most stably generated $H^+(H_2O)n$ as the positive ion and $O_2^-(H_2O)n$ as the negative ion.

When these ions are generated, hydrogen peroxide $H_2O_2$, or the radical .OH, which are active species, are generated by chemical reactions. Hydrogen peroxide $H_2O_2$ or the radical .OH exhibits very strong activity and hence is able to sterilize and remove microorganisms floating in the air.

Further, it is also possible to use a gas mainly containing either the positive or negative ions as the particles for sterilizing the microorganisms. In this case, there can be generated an effect that the sterilizing action is effected in such a manner that the cell or the surface protein of the microorganism is destroyed by the electrical action to the microorganism due to the electric charges of the ions.

It is possible to use ozone or a radical as the particle for sterilizing the minute substance, particularly the microorganism. The ozone or the radical, which has an excellent ability to sterilize the microorganism, is able to effectively remove the microorganism. After exhibiting the sterilizing ability, the ozone becomes harmless oxygen and is not left as it is. Also, the radical is combined with the floating microorganism or various molecules in the air to become an inert substance. As a result, the ozone and the radical are made harmless with time and are not left as they are. Thus, it is possible to evaluate the ability to sterilize the microorganism by using the ozone or the radical.

Further, it is also possible to use a medical agent to sterilize the microorganism and possible to perform the sterilizing treatment by irradiating the particles of the medical agent. When the sterilizing treatment is performed by using the medical agent, it is possible to supply the particles of the chemical agent by a simpler apparatus as compared with the case where the ion or ozone is used. Thus, it is possible to evaluate the ability to remove the minute substance by using the medical agent.

Note that the above described method can be particularly suitably used for a test method in which charged particles, radicals, or particles having a sterilizing ability are used as the removal particles. In the test in which charged particles, radicals, or particles having a sterilizing ability are discharged in the air to verify the effect of the discharged particles, the test is generally performed by discharging the particles in an amount range harmless to the human body in view of the application to ordinary households. Therefore, in order to investigate the effect of such particles in removing the microorganisms in the air, it is necessary to investigate the effect of removing the floating microorganisms for a comparatively long time. In this case, it is necessary to make the microorganisms stably float for a long time. Thus, the above described method is significantly effective and is suitable for the evaluation of the charged particles, radicals, or particles having the sterilizing ability in the air.

As for the measurement of the minute substance, there can be listed the measurement of concentration of the minute substance. Further, the measurement of the microorganism is the measurement of microorganism concentration, the measurement of cell infection rate, or the measurement of allergic reaction. Thereby, it is possible to perform the microorganism removal evaluation.

Further, when the collected microorganism is measured, it is also possible to measure the time-sequential change in the microorganism with respect to the irradiation time of the particles. Thereby, it is possible to quantitatively evaluate the ability to sterilize the microorganism with respect to the lapse of time.

Further, when the collected microorganism is measured, it is also possible to measure the concentration dependency of the removal particles. Thereby, it is possible to quantitatively evaluate the ability to sterilize the microorganism with respect to the concentration dependency of the removal particles.

Further, for the above described evaluation method, it is possible to use the cell culture by microorganisms, the erythrocyte agglutination by microorganisms, or the allergic reaction by microorganisms. Thereby, it is possible to evaluate the activity or the concentration of microorganisms.

Advantages of the Invention

According to the present invention, it is possible to more accurately and stably perform the environmental evaluation test for sterilization, deodorization, and the like, of minute substances.

Further, it is possible to make microorganisms stably float by preventing the spontaneous disappearance of the microorganisms. Thereby, it is possible to stably perform the environmental evaluation test for sterilization, deodorization and the like.

BRIEF DESCRIPTION OF THE DRAWINGS

FIG. 3 shows a configuration of isolation walls of an evaluation chamber of the environmental evaluation installation according to the first embodiment, in which FIG. 3(a) is a sectional view and FIG. 3(b) is a front view seen from the inner wall side;

DESCRIPTION OF SYMBOLS

Figure 1:
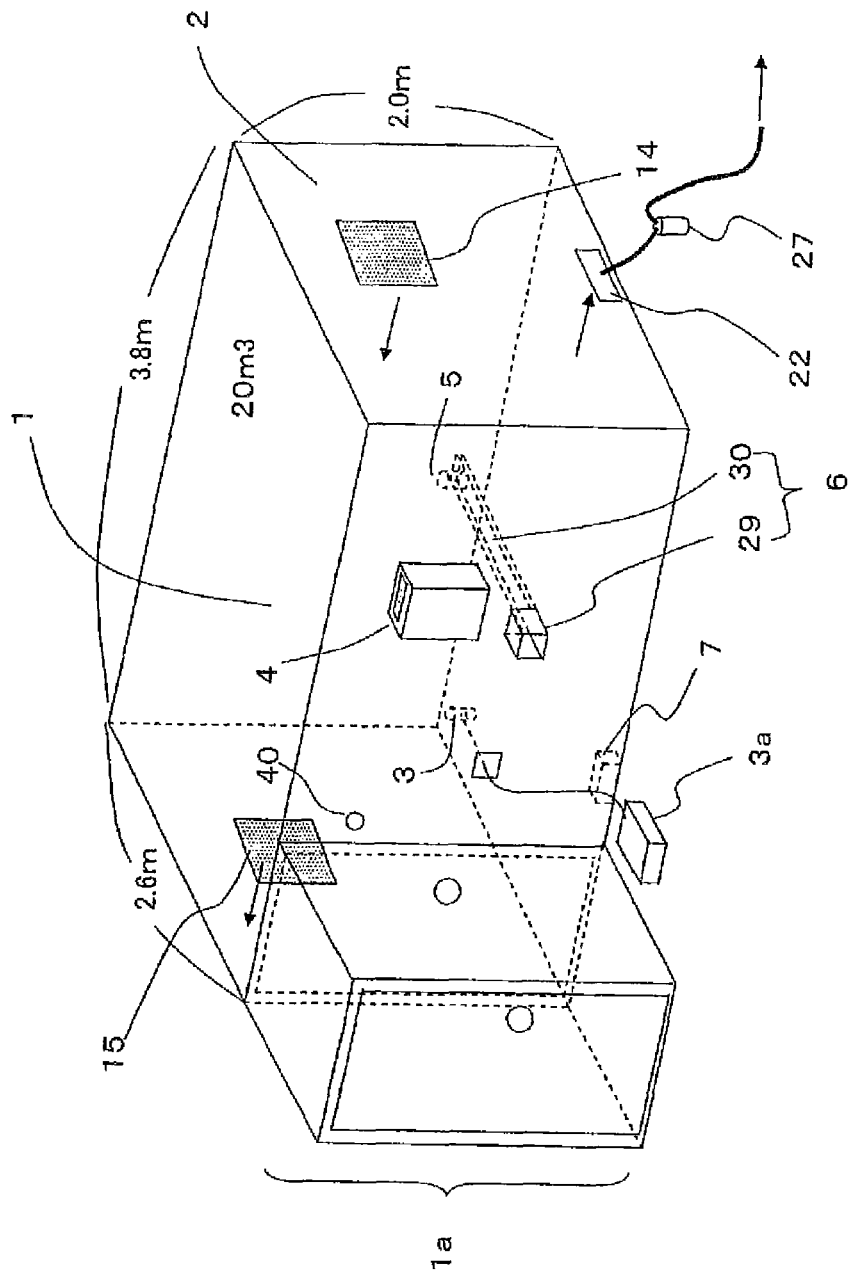
FIG. 1 is a figure showing a schematic configuration of an environmental evaluation installation according to a first embodiment.
Figure 2:
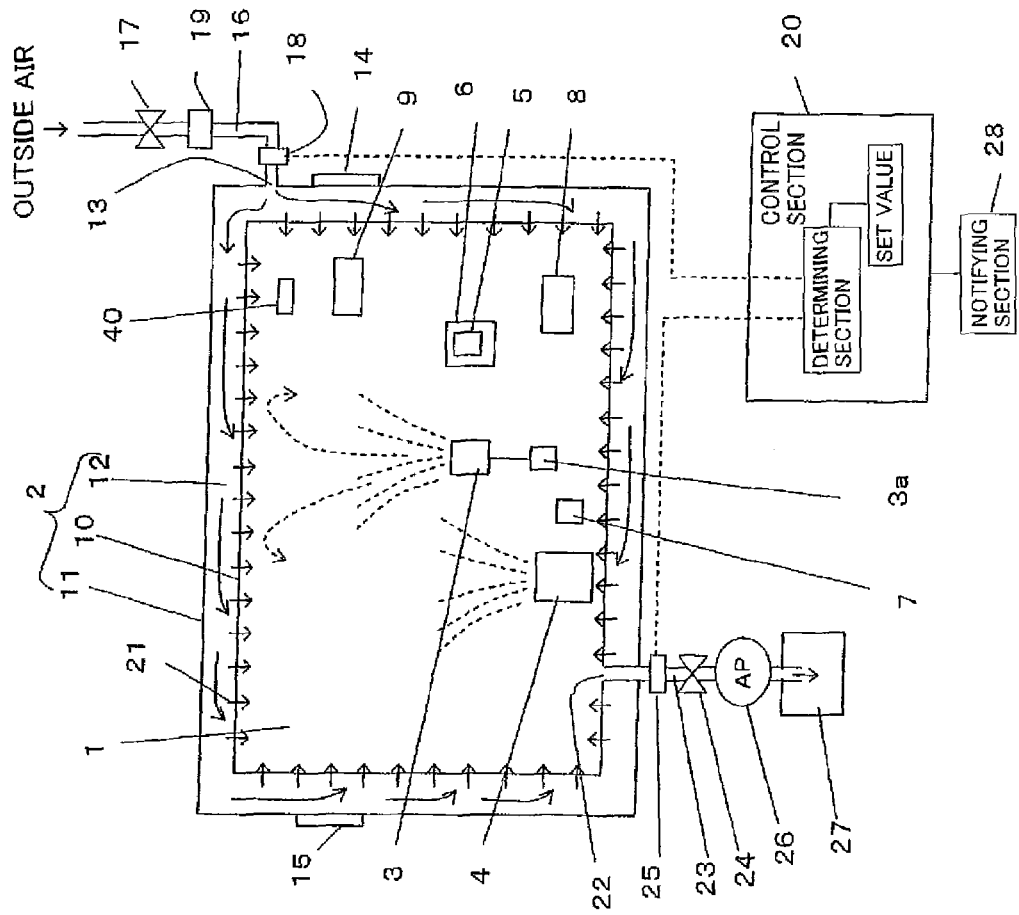
FIG. 2 is a figure showing air flows in the environmental evaluation installation according to the first embodiment.
Figure 3:
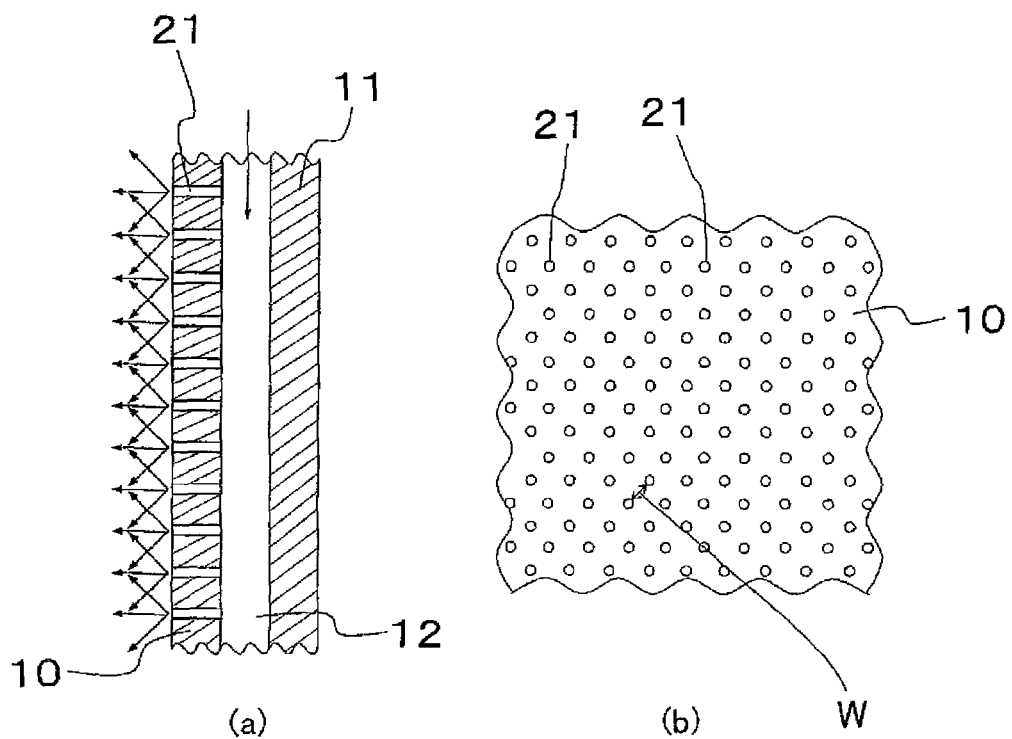

1 Evaluation chamber
1a Double door
2 Isolation wall
3 Nebulizer
4 Air cleaning apparatus
5 Air sampler
6 Taking in and out mechanism
8 Humidifier
10 Inner wall
11 Outer wall
12 Air flow passage
13 Air intake opening
16 Air supply pipe
18 Inflow amount measuring section
19 Heater
20 Control section
21 Air supply hole
22 Air exhaust opening
23 Exhaust pipe
25 Exhaust amount measuring section
26 Pump apparatus
27 Impinger
28 Notifying section
29 Pass box
30 Moving means
33 Rail
34 Movable body
39 Pump apparatus
41 Rail
42 Movable body
12 Cleaning means
13 Filter net
14 Filter frame
15 Rib
17 Side wall
18 Central body
19 Guide piece
20 Stopper
21 Inner rail
22 Outer rail
23 Side plate
24 Front plate
25 Rotating section
26 Locking section
27 Projecting section
28 Locking hole
29 Partitioning wall
30 Motor
34 Suction section
35 Suction apparatus
36 Suction duct

BEST MODE FOR CARRYING OUT THE INVENTION

In the following, embodiments according to the present invention will be described.

First Embodiment

The environmental evaluation installation includes a series of mechanisms which are configured to set the inside of an evaluation chamber to a negative pressure, which are configured to make microorganisms serving as an evaluation object uniformly float in the evaluation chamber by spraying and stirring the microorganisms, and which are configured, after performing treatment to the microorganisms in the floating state by removal particles, to perform analysis and evaluation by sampling the microorganisms.

Further, the environmental evaluation installation is characterized in that the wall effect in the evaluation chamber is eliminated. Thereby, it is possible to improve the instability in the evaluation test which instability is caused by the action between the microorganisms floating in the evaluation chamber and the wall surface of the evaluation chamber Since the microorganisms are made to stably float in the air, a highly precise test is realized.

Further, the environmental evaluation installation, in which the air in the evaluation chamber is sucked to the outer space in order to hold the inside of the evaluation chamber in the negative pressure state, is characterized in that the air exhaust amount is fixed. Since the exhaust amount of the microorganisms is fixed, the removal evaluation of the microorganism can be performed under the same condition at any time.

Further, the environmental evaluation installation is characterized by including a taking in and out mechanism for taking minute substance collecting means in and out of the evaluation chamber. The minute substance collecting means needs to be exchanged in order to investigate the time-sequential change of the microorganisms. However, by using the taking in and out mechanism, it is possible to eliminate the need of a person to go in and out of the evaluation chamber to exchange the minute substance collecting means. Thereby, it is possible to prevent the leakage and entering of the microorganisms.

Further, the environmental evaluation installation is characterized in that spore-forming bacteria (*Bacillus subtilis*) in a sporulated state are used as the microorganism in order to prevent the spontaneous disappearance of the microorganism.

In the following, the present invention will be described in more detail by means of more specific embodiments, but the present invention is not limited to these. Note that in the following, the embodiments are described with reference to the accompanying drawings, but the same or corresponding portions are denoted by the same reference numerals or characters in the accompanying drawings according to the present invention. Further, an arrow shows an air flow.

FIG. 1 is a figure showing a schematic configuration of an environmental evaluation installation according to a first embodiment. FIG. 2 is a figure showing air flows in the environmental evaluation installation according to the first embodiment. As shown in FIG. 1 and FIG. 2, the environmental evaluation installation includes: an evaluation chamber 1 isolated by isolation walls 2 from outer space; minute substance supply means 3 configured to supply microorganisms into the evaluation chamber 1; an air cleaning apparatus 4, as minute substance removing means, configured to supply into the evaluation chamber 1 removal particles for sterilizing and removing the microorganisms; and minute substance collecting means 5 configured to collect the microorganisms in the evaluation chamber 1, and is configured to measure and evaluate the microorganism corrected by the minute substance collecting means from 5. Further, the environmental evaluation installation includes a taking in and out mechanism 6 for taking the minute substance collecting means 5 in and out of the evaluation chamber 1.

The evaluation chamber 1 is isolated from the outer space in all directions by the isolation walls 2, and the portion of the evaluation chamber 1 other than air supply holes 21 as will be described below is configured as a clean room having high airtightness. The space size of the evaluation chamber 1 is set to about 20 $m^3$ (dimensions between the inner wall 10 surfaces are shown in the figure), but the size is not limited to this. Further, a double door 1*a* for entrance/exit of the user is provided in a part of the evaluation chamber 1. Further, a stirring fan 7 is provided in a lower part of the evaluation chamber 1. The stirring fan 7 is able to stir the space by forming an air flow around itself, so as to prevent the natural sedimentation of the microorganism to the lower part of the evaluation chamber 1 due to the weight of the microorganism itself. Thereby, it is possible to increase the microorganisms floating in the region in which the removal particles generated by the air cleaning apparatus 4 effectively exist. Therefore, it is possible to effectively perform the sterilizing treatment by the removal particles. Further, in the evaluation chamber 1, an ultrasonic humidifier 8 is installed as a first air conditioning section to adjust the humidity. Further, a germicidal lamp 9 is provided so that the inside of the evaluation chamber 1 can be sterilized. The germicidal lamp 9 is mainly used to sterilize the inside of the evaluation chamber 1 before an evaluation test is started. Further, there is provided a barometer 40 for measuring the atmospheric pressure in the evaluation chamber 1.

The isolation wall 2 is configured by an inner wall 10, an outer wall 11, and an air flow passage 12 formed between the inner wall 10 and the outer wall 11. A paint baking type steel sheet which is a standard wall surface material of the evaluation chamber 1 is adopted for the inner wall 10 and the outer wall 11. Note that a vinyl chloride based flooring material is used for the floor surface among the inner walls 10. The inside of the evaluation chamber 1 is designed so as to be in a weak negative pressure state, and hence is configured to prevent the leakage of bacteria to the outside. The inside of the evaluation chamber 1 is designed to match with the reference level 2 in the biological test.

In the outer wall 11, there is provided an air intake opening 13 for taking the air into the air flow passage 12 from the outer space. As ventilation openings for ventilating before and after an evaluation test, there are provided an air intake ventilation opening 14 and an air exhaust ventilation opening 15. The air intake ventilation opening 14 and the air exhaust ventilation opening 15 can be closed, and are closed during the evaluation test.

A HEPA/activated carbon filter is provided in the air intake opening 13 and the air intake ventilation opening 14, so that the cleaned air can be introduced. Further, the HEPA/activated carbon filter is also provided in the air exhaust ventilation opening 15, so that the cleaned air can be exhausted to the outer space. Note that the filter provided in the air intake opening 13 and the air exhaust opening 22 is not limited to the HEPA/activated carbon filter, and the other kind of filter may be used.

An air supply pipe 16 is connected to the air intake opening 13. A valve 17 for opening and closing the inside of the air supply pipe 16, an inflow amount measuring section 18, and a heater 19 as a second air conditioning section for adjusting the temperature are provided for the air supply pipe 16. The inflow amount measuring section 18 is a flowmeter, and detects the amount of the air passing through the air supply pipe 16, that is, detects the inflow amount, and notifies the detected amount to a control section 20.

The heater 19 adjusts the temperature of the air passing through the air supply pipe 16 to a suitable temperature. The temperature-adjusted air is introduced into the evaluation chamber 1 from the respective air supply holes 21 as will be described below through the air flow passage 12. Generally, in the case where the substance made to float is liquid such as solution particles containing bacteria as in the present embodiment, as the temperature of the air introduced from the air supply holes 21 is increased, it is more possible to prevent the solution particles from adhering to the wall surface due to dew condensation. In the present embodiment, the inner wall 10 per se may also be configured to be able to be heated.

As shown in FIG. 3(*a*) and FIG. 3(*b*), the many air supply holes 21 are provided over almost the whole surfaces of the inner walls 10 except the floor surface. It is configured such that the air in the outer space, after passing through the air flow passage 12 from the air intake opening 13, can flow into the evaluation chamber 1 from the air supply holes 21. The air supply hole 21 is a pore having a diameter of 0.1 to 2 cm, and the distance W between the adjacent holes is set to approximately one to three times the diameter of the hole. With this configuration, the whole wall surfaces are covered with the air ventilated to the inside of the evaluation chamber 1, and further, a part of the air ventilated from the each air supply hole 21 is made to intersect with a part of the air ventilated from the other nearest air supply hole 21. In the present embodiment, the diameter of the hole is set to approximately 0.2 mm and the distance between the adjacent holes is set to approximately 0.4 mm.

Further, an air exhaust opening 22 for exhausting the air in the evaluation chamber 1 is provided in the inner wall 10. An exhaust pipe 23 is connected to the air exhaust opening 22. The exhaust pipe 23 is made to pass through the air flow passage 12 and the outer wall 11, so as to be opened to the outer space. In the exhaust pipe 23, there are provided a valve 24 for opening and closing the inside of the pipe, an exhaust amount measuring section 25, a pump apparatus 26 as suction means for sucking the air in the evaluation chamber 1 to maintain the inside of the evaluation chamber in the negative pressure state, and an impinger 27 as in-exhaust minute substance collecting means.

It is configured such that the exhaust air exhausted from the air exhaust opening 17 is discharged to the outer space after being cleaned by a filter, and the like, via the impinger 27. Since the total amount of the air introduced per unit time from the respective air supply holes 21 is designed to be sufficiently smaller than the volume of the evaluation chamber 1, the amount of the exhaust air from the air exhaust opening 17 is also small, and hence the influence of the exhaust air on the air flow caused by the stirring in the evaluation chamber 1 is very small. However, when a highly precise test condition is required, there is performed a correction based on the amount of the exhaust air from the air exhaust opening 17 and the number of bacteria collected in the impinger 27. Note that the impinger 27 may be omitted.

The exhaust amount measuring section 25 is a flowmeter and detects the amount of the air passing through the exhaust pipe 23, that is, the amount of air exhausted from the evaluation chamber 1, and notifies the detected amount to the control section 20. On the basis of the detected exhaust amount, the control section 20 controls the pump apparatus 26 so as to fix the exhaust amount.

Here, the exhaust amount is an important factor in the evaluation test of microorganisms. This is because, as the amount of air exhausted from the evaluation chamber 1 is increased, the amount of microorganisms discharged together with the air is increased. When the amount of microorganisms used as a base substance is changed between comparative tests due to the change in the exhaust amount, it is not possible to perform accurate evaluation. Thus, when the exhaust amount is fixed, it is possible to perform the evaluation under the same condition. Thereby, it is possible to improve the precision of the evaluation. According to this method, it is possible to obtain a value from which the decrease of the microorganism is subtracted, and hence it is possible to measure the performance of the air cleaning apparatus 4 itself.

Note that in the above described embodiment, the control section 20 is configured to perform control so that the exhaust amount is always fixed, but the control section 20 may also be configured to perform control so that the time-sequential change in the exhaust amount in the case where the microorganism is not removed is equal to the time-sequential change in the exhaust amount in the case where the microorganism is removed. It is possible to perform both the evaluation tests under the same condition.

Further, the control section 20 determines in a determining section whether or not the air flow in the evaluation chamber is normal, on the basis of the difference between the exhaust amount from the exhaust amount measuring section 25, and the inflow amount from the inflow amount measuring section 18. For example, when the exhaust amount is smaller than the inflow amount, and when the difference between the exhaust amount and the inflow amount is larger than a predetermined value, it is estimated that a leakage of air from the evaluation chamber 1 is caused. In such a case, a warning is issued by a notifying section 28. As for the form of the notifying section 28, there are listed a display in a display section, such as a monitor, and notification by sound or light.

As the minute substance supply means, there is used Nebulizer 3 (NE-C16 made by OMRON Co., Ltd.) which is capable of spraying a microorganism solution. Nebulizer 3 has an air pump 3a, and is configured such that an aqueous solution is discharged into the space from a nozzle by being changed to particles having a size of about 1 to 10 μm by the air compressed by the air pump 3a. Note that it is possible to arbitrarily adjust the concentration of bacteria and the amount of solution of the concentration, which can be filled in the air pump 3a. The solution containing bacteria is changed to liquid fine particles by being filled in a filling solution pool, so as to be discharged to the space.

Now, there will be described the microorganism used here.

The used microorganism is *Bacillus subtilis* in a sporulated state, which belongs to the genus *Bacillus*. *Bacillus subtilis*, which is bacteria generally existing in the nature and is an aerobic Gram-positive *bacillus*, forms a spore depending on conditions.

The spore is a structure of a cell whose structure exhibits high durability to heat, a chemical, and the like. In an ordinary growing state, the spore-forming bacteria are in the nutritional state and do not form a spore. However, when put in a poor nutritional state, the spore-forming bacteria form a spore and are changed to a state extremely suitable for being preserved.

The *Bacillus subtilis* does not generally have pathogenicity against humans.

Next, there will be described a method for making the *Bacillus subtilis* (spore) which is used. In this case, the *Bacillus subtilis* used as original bacteria is applied on a SCD agar medium, and is cultured for about one week at 37° C. The nutritive substance on the agar medium is depleted by such long-time culturing, and thereby *Bacillus subtilis* is changed to a spore, so as to be in a gel-like membrane state.

A solution containing only the *Bacillus subtilis* spore is created in such a manner that the membrane is removed by a spatula and is stirred and centrifuged in a test tube in which a phosphoric acid buffer solution is housed, and further is subjected to heat treatment for 5 minutes at a temperature of 95° C.

Further, the air cleaning apparatus 4 as the minute substance removing means is a type which uses ions generated by an electric discharge in the air and emits positive and negative ions, and which realizes the sterilizing or deodorizing effect by the oxidation performance based on the energy of the emitted ions.

Note that on the discharge electrodes in the present embodiment, there are generated ions which contain, as main components, $H^+(H_2O)m$ as positive ions, and $O_2^-(H_2O)n$ as negative ions (where m and n are natural numbers). However, generally, as for ions emitted from the discharge electrodes, various ions can be emitted by adjusting the discharge conditions such as, for example, the discharge voltage and the electrode structure. Thus, the kinds of the positive ions are not limited to only $H^+(H_2O)m$, but may include, for example, $H_2O^+$, $H_3O^+$, $N_2^+$, $O_2^+$, $CO_2^+$, and the like. Further, similarly, the kinds of the negative ions are not limited to only $O_2^-(H_2O)n$, but may include, for example, $OH^-$, $H_2O^-$, $O_3^-$, $O_2^-$, $N_2^-$, $NO_2^-$, $NO_3^-$, $CO_2^-$, $CO_3^-$, and the like. These ions can be used in the present test technique.

Figure 4:
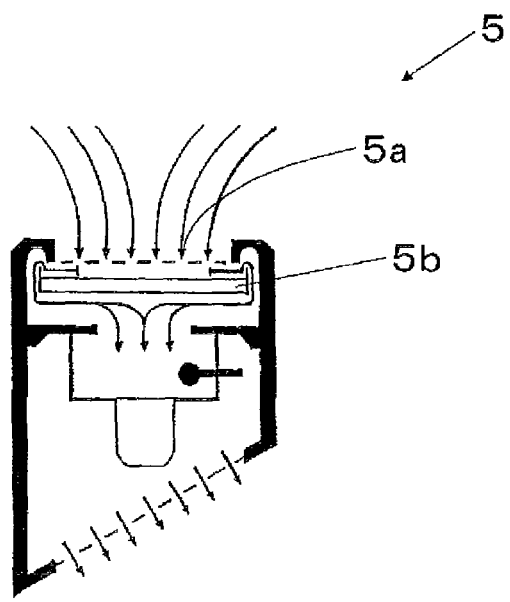
FIG. 4 is a figure showing the principle of an air sampler (MAS-100 manufactured by Merck Co. Ltd.)

As the minute substance collecting means for collecting floating bacteria, the air sampler 5 (MAS-100 made by Merck Co. Ltd.) is used. The air sampler 5 is a system referred to as the Andersen system. The air sampler 5 is able to collect about 100% of particles having a size of 1 μm or more, in such a manner that as shown in the principle figure of FIG. 4, bacteria (or particles) in the air are sucked and made to pass through a hole 5a, so as to be stricken onto a culture medium 5b. Note that the bacteria stuck to the culture medium 5b grow by being preserved in a suitable temperature environment (for example, 30° C.), and can be observed as a colony in about one day.

Note that there is a case where a plurality of bacteria made to pass through one hole are counted as one colony, and hence the observed coefficient value is corrected by a conversion table created beforehand.

Figure 5:
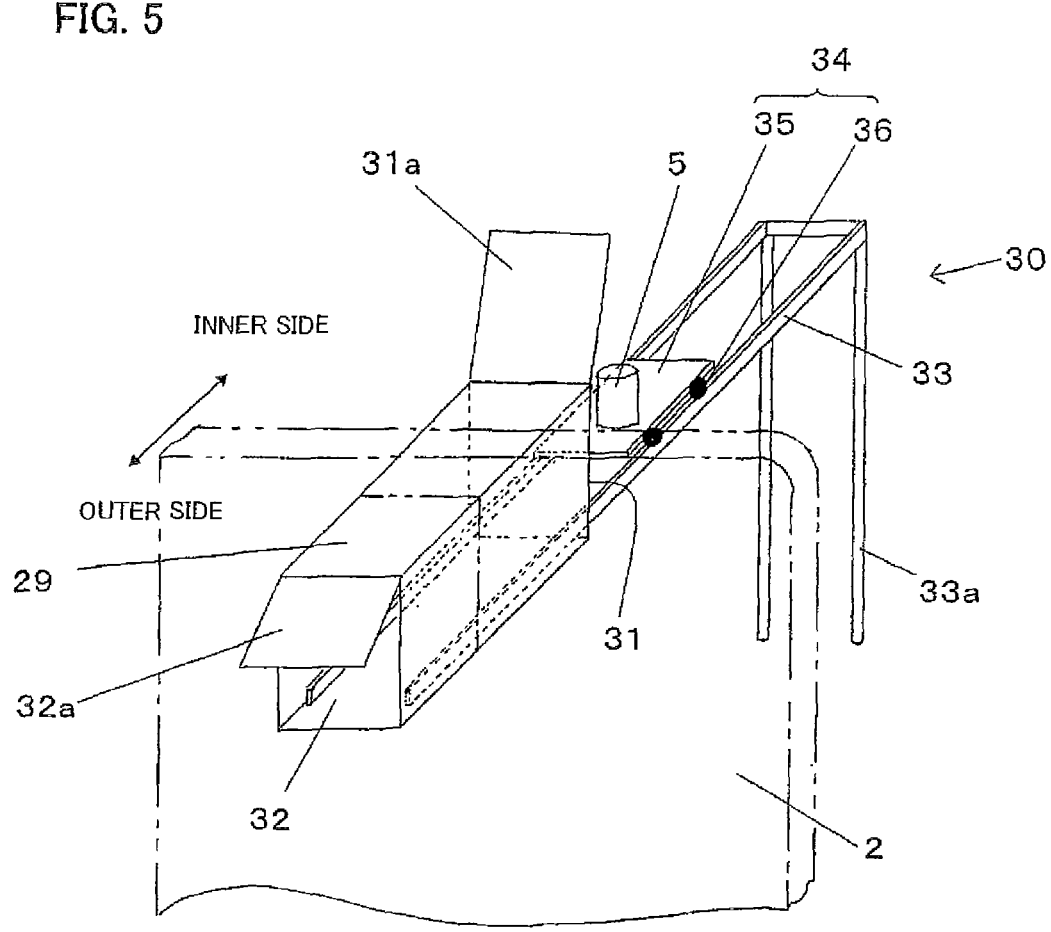
FIG. 5 is a figure showing a schematic configuration of a taking in and out mechanism 6 of the air sampler of the environmental evaluation installation according to the first embodiment.

Further, as shown in FIG. 5, there is provided the taking in and out mechanism G for taking the air sampler 5 in and out the evaluation chamber 1. The taking in and out mechanism 6 is configured by a rectangular parallelepiped shaped pass box 29, and moving means 30 configured to be able to move the air sampler 5 between the pass box 29 and a predetermined position inside the evaluation chamber 1.

The pass box 29, which is a container body fixed so as to penetrate the isolation wall 2, has one side openable in the evaluation chamber and the other side openable in the outer space. Doors 31a and 32a which can be closed in an openable and closable manner are respectively provided at an opening 31 on the side of the evaluation chamber and at an opening 32 on the side of the outer space. Further, among the door 32a on the side of the outer space and the door 31a on the side of an evaluation chamber, at least the door 31a on the side of the evaluation chamber can be automatically opened and closed by controlling fluid pressure by a cylinder (not shown), and the like. The opening and closing operation of the door 31a is performed by a remote operation.

The moving means 30 is configured by rails 33 serving as a guide passage provided between the predetermined position in the pass box 29 and the predetermined position in the evaluation chamber 1, and a movable body 34 on which the air sampler 5 is mounted and which is moved along the rails 33.

The rails 33 are provided from the bottom surface of the pass box 29 so as to reach the predetermined position in the evaluation chamber 1, and are fixed to the floor surface of the evaluation chamber 1 by a plurality of legs 33a.

The movable body 34 is configured by a mounting table 35 serving as the mounting surface of the air sampler 5 and wheels 36 provided on the bottom surface of the mounting table 35. The wheels 36 are fitted to the rails 33 and are movable along the rails 33. Further, the mounting table 35 has a driving section (not shown) for driving the wheels 36, and a receiving section (not shown) which can be remotely operated, so that the drive of the wheels 36 is remotely controlled. The movable body 34, on which the air sampler 5 is mounted, can be freely moved back and forth along the rails 33 by the remote operation.

Note that in the above, the rails 33 are used as the guide passage, but a conveyor belt may also be used instead of the rails 33. In the case of the conveyor belt, it is not necessary to provide the wheels 36 and the receiving section in the movable body 34. The movable body 34 can be moved by controlling the rotational drive of the conveyor belt.

In the following, there will be described a test procedure using the environmental evaluation installation having the above described configuration.

(1) Preparation of Test

Before the test is started, the air intake ventilation opening 14 and the air exhaust ventilation opening 15 are operated so that the inside of the chamber is filled with clean air with little dust.

Further, it is preferred that the wall surfaces, and the like, inside the evaluation chamber 1 are sterilized beforehand by being irradiated with ultraviolet rays generated by the germicidal lamp 9 for a fixed time. Further, it is preferred that the humidity of the air in the evaluation chamber 1 is adjusted by the ultrasonic humidifier 8 provided in the evaluation chamber 1.

After the sterilization of the inside of the evaluation chamber 1 is completed, the operation of the air intake ventilation opening 14 and the air exhaust ventilation opening 15 and the operation of the germicidal lamp 9 are stopped.

(2) Spraying of Bacteria

Next, a bacteria solution is sprayed into the evaluation chamber 1 by the Nebulizer 3. It is assumed that at this time, the air is blown by the stirring fan 7 so that the sprayed bacteria can be spread into the space. Further, it is possible to select a method in which the spaying is performed, for example, for about 10 minutes.

In this case, the air whose temperature is adjusted by the heater 19 is taken in from the air intake opening 13 in such a manner that the valve 24 of the exhaust pipe 23 and the valve 17 of the air supply pipe 16 are opened, and that a substantially fixed amount of the air in the evaluation chamber 1 is always sucked and exhausted by the pump apparatus 26. The air taken in from the air intake opening 13 is made to flow into the evaluation chamber 1 from the air supply holes 21 of the inner walls 10 through the air flow passage 12, so that air flows are formed near the surfaces of the inner walls 10. The air flows make it possible to prevent the sprayed bacteria from adhering to the surfaces of the inner walls 10 of the evaluation chamber 1.

At this time, the amount of inflow and exhaust of the air to and from the evaluation chamber 1 are set to a very small amount. Specifically, the air exhaust amount is set to 10 m$^3$/hour, and the set air exhaust amount is maintained during the evaluation test. Such control is performed in such a manner that the control section 20 controls the pump apparatus 26 on the basis of a signal of the exhaust amount detected by the exhaust amount measuring section 25. Further, on the basis of the air pressure data from the barometer 40, the control section 20 controls the valve 17 provided in the air supply pipe 16 so that the pressure in the evaluation chamber 1 is slightly lower than the pressure outside the evaluation chamber 1 by about 1/10000 atmospheres. Since the inside of the evaluation chamber 1 is maintained at a weak negative pressure by this method, it is possible to prevent the floating bacteria from being leaked to the outer space.

Further, the control section 20 determines in the determining section whether or not the air flow in the evaluation chamber 1 is normal, on the basis of the difference between the exhaust amount from the exhaust amount measuring section 25 and the inflow amount from the inflow amount measuring section 18. When the air flow in the evaluation chamber 1 is abnormal, a warning is issued by the notifying section 28. Specifically, when the exhaust amount is smaller than the inflow amount and when the difference between the exhaust amount and the inflow amount is larger than a predetermined value, it is estimated that a leakage of air from the evaluation chamber 1 is caused, and hence a warning is issued by the notifying section 28.

(3) Collection of Bacteria

The air sampler 5 is moved into the evaluation chamber 1, so as to collect the bacteria floating in the evaluation chamber 1. Note that the collection of the floating bacteria is performed every 10 minutes, and is performed a total of 7 times in 60 minutes. Thereby, the time-sequential change in the concentration of the floating bacteria is measured.

The collecting method is specifically performed as follows. The door 32a on the side of the outer space of the pass box 29 is opened, and the air sampler 5 provided with the agar medium 5b is mounted on the movable body 34. Then, the door 32a on the side of the outer space is closed.

Then, the door 31a on the side of the evaluation chamber is opened by the remote operation, and the movable body 34 is moved to reach the predetermined position in the evaluation chamber 1. The door 31a on the side of the evaluation chamber is closed. Next, the air sampler 5 is operated by a timer function or a remote control operation, so as to collect the floating bacteria in the evaluation chamber 1.

Further, the air sampler 5 is taken out as follows. The door 31a on the side of the evaluation chamber is opened by the remote operation and the movable body 34 is moved to the inside of the pass box 29. Thereafter, the door 31a on the side of the evaluation chamber is closed. Then, when the door 32a on the side of the outer space is opened, it is possible to take out the air sampler 5 in which the floating bacteria are collected.

(4) Drive of Air Cleaning Apparatus 4

The air cleaning apparatus 4 is operated. Here, it is possible to select a method in which the operation of the air cleaning apparatus 4 is started, for example, at the time when the collection of bacteria is performed at first. The ions emitted from the air cleaning apparatus 4 are capable of sterilizing bacteria by colliding and reacting with the bacteria, so as to reduce the amount of bacteria floating in the evaluation chamber 1.

(5) End

When the collection of floating bacteria is ended, the air cleaning apparatus 4 is stopped, and the clean air is introduced into the evaluation chamber 1 so as to exhaust the air containing the floating bacteria to the outside.

With the above described configuration, the bacteria or the solution particles, which are made to float in the evaluation chamber 1, are significantly prevented from colliding and adhering to the wall of the evaluation chamber 1. Thus, even when the test is performed a plurality of times, the test can be stably performed in the state where the statistical variation in the collected results is small, without depending on the concentration of the bacteria or the solution particles which are made to float in the evaluation chamber 1.

Further, since the air exhaust amount is kept constant, it is possible to eliminate the variation in the amount of decrease of the floating bacteria due to the exhausting of the air, and thereby it is possible to acquire stable test data. Further, it is possible to prevent the floating bacteria from being leaked to the outside of the evaluation chamber 1 by setting the inside of the evaluation chamber 1 to a negative pressure. Further, it is possible to determine the leakage of the air from the evaluation chamber 1 by detecting the inflow amount of the air, so that a safer environmental evaluation installation can be realized.

Further, as for the collection of the floating bacteria, it is possible to eliminate the need of a person going in and out to exchange the air sampler 5, by providing the taking in and out mechanism 6. Thereby, it is possible to improve the safety and possible to prevent floating bacteria from entering from the outer space, Thus, it is possible to improve the precision in the evaluation.

Next, there will be described examples of test results obtained by the present test installation.

[Removal Effect Test]

Figure 6:
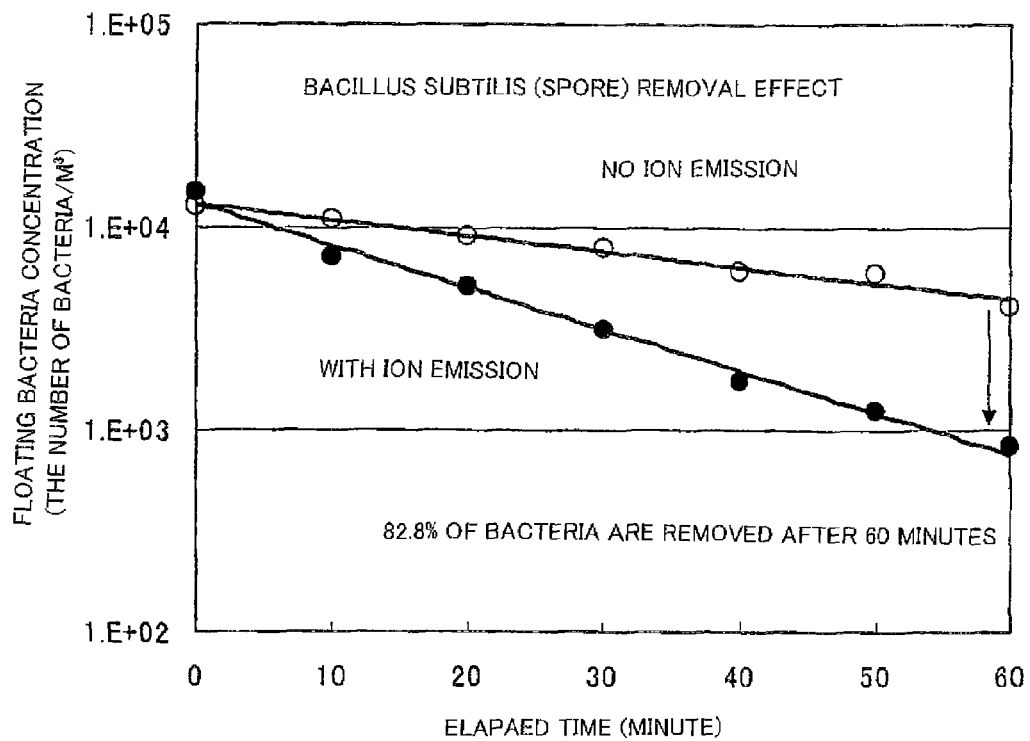
FIG. 6 is a figure showing results of removal effect tests.

FIG. 6 is a figure in which the ordinate represents the concentration of floating bacteria in the evaluation chamber 1 having *Bacillus subtilis* floating therein and having a volume of 20 m$^3$, and which shows time-sequential changes in the concentration of the floating bacteria. In the test results, in the case where the ions (removal particles) are emitted, about 83% of the floating bacteria are removed after 60 minutes as compared with the case where the ions are not emitted. Even when the test was performed a plurality of times under the same condition, it was confirmed that the tests were stably performed so that the inclination of the approximate lines of respective plots was controlled to a variation range of 10% or less.

[Stability Test of *Bacillus Subtilis*]

The change in the number of bacteria was evaluated in the state where *Bacillus subtilis* in a sporulated state and *Bacillus subtilis* in a nutritional state were used, where the relative humidity was set to 32%, and where the ions (removal particles) are not emitted. The evaluation results are shown in FIG. 7.

Figure 7:
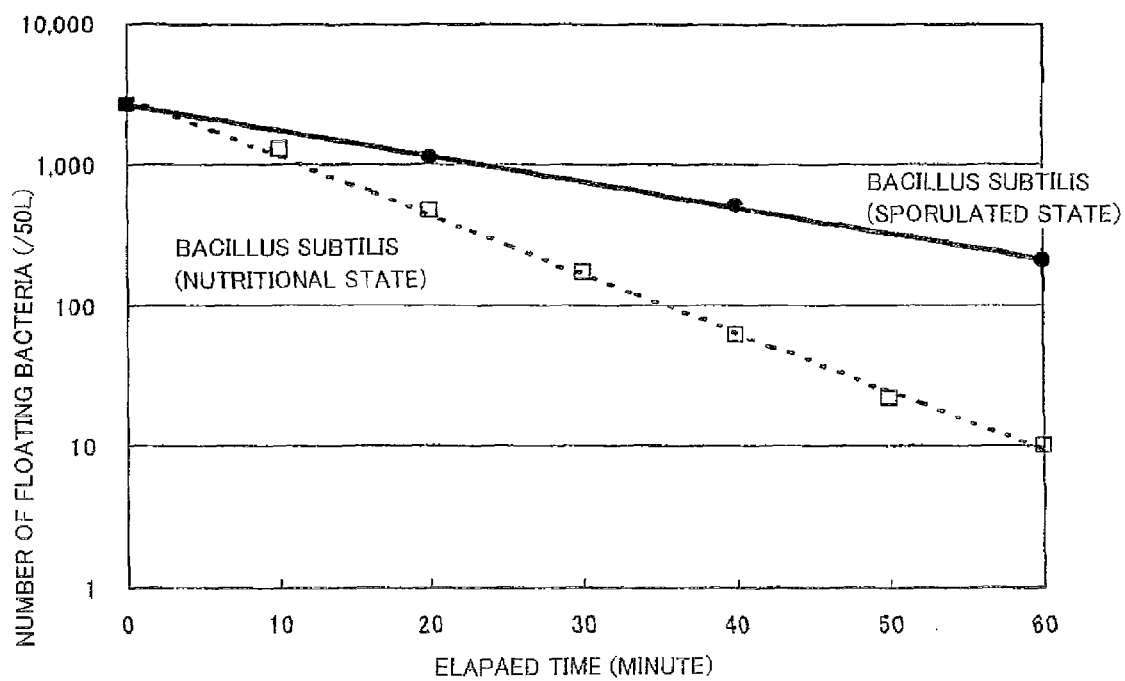
FIG. 7 is a figure showing results of stability tests of *Bacillus subtilis*.

In FIG. 7, it is seen that the number of *Bacillus subtilis* (in the nutritional state) was significantly reduced to about $\frac{1}{100}$ or less after 60 minutes. On the other hand, it is seen that the number of *Bacillus subtilis* (in the sporulated state) was insignificantly reduced to $\frac{1}{10}$ after 60 minutes. It is estimated that the spore of *Bacillus subtilis* is resistant to drying and hence is unlikely to become extinct even in the low humidity environment in which the relative humidity is about 30%, so that the *Bacillus subtilis* in the sporulated state can be made to float in living state for a long time.

In this way, in the environmental evaluation installation according to the present invention, it is possible, by using the spore of *Bacillus subtilis*, to float the bacteria in living state for a long time. Therefore, it is possible to perform a highly precise test without receiving the influence of humidity.

[Humidity Test]

In the above described stability test of *Bacillus subtilis*, the spore-forming bacteria in a sporulated state were used as the microorganism in order to prevent the spontaneous disappearance of the microorganism. However, the present test is characterized in that the humidity in the evaluation chamber 1 is controlled to 45% or more in order to prevent the spontaneous disappearance of the microorganism, and the other fundamental configuration in the present test is the same as that of the above described stability test of *Bacillus subtilis*. Note that *Escherichia coli* is used as the microorganism in the present test.

Specifically, the relative humidity in the evaluation chamber 1 is controlled to 45% or more by using the ultrasonic humidifier 8 provided in the evaluation chamber 1.

Figure 8:
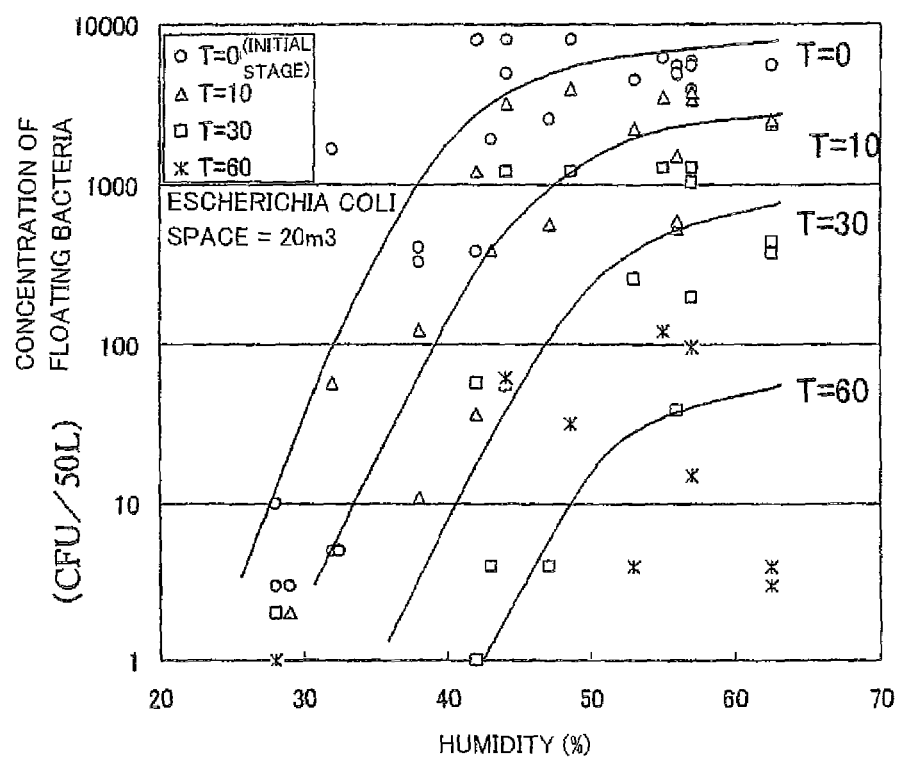
FIG. 8 is a figure showing results of humidity tests.

FIG. 8 shows the results which were obtained by investigating the correlation between the relative humidity and the amount of floating *Escherichia coli*, and which were obtained by investigating the number of floating live bacteria at 0, 10, 30 and 60 minutes after the change of the relative humidity in the evaluation chamber 1. Note that CFU is the abbreviation for "colony forming unit".

As can be seen from FIG. 8, the amount of floating *Escherichia coli* can be kept to a large amount by setting the relative humidity to 45% or more.

In this way, in the floating microorganism test method according to the present invention, the test is performed by spraying *Escherichia coli* in the state where the humidity is controlled, and thereby it is possible to float the bacteria in living state for a long time.

Note that in the present test, *Escherichia coli* is used as the microorganism, but it is possible to perform the evaluation by using the other microorganism.

Note that the present invention is not limited to the above described embodiment, but numerous modifications and changes can be obviously made therein without departing from the spirit and scope of the present invention. For example, in the above described embodiment, the ions are used for the sterilizing method, but it is possible to select various chemical substances, such as ozone, plasma, and a radical. Further, in the above described embodiment, *Bacillus subtilis* or *Escherichia coli* is used as the minute substance, but it is possible to perform the evaluation by using microorganisms in the concept including other bacteria, fungi (including mold), viruses, allergen substances (including ticks), and the like, house dust, powder dust, pollen, malodor, and harmful chemical substances.

Further, in the above described embodiment, the isolation wall 2 of the evaluation chamber 1 is configured by the inner wall 7, the outer wall 8, and the air flow passage 9, and a plurality of air supply holes 10 are provided in the inner wall 7. However, the isolation wall 2 of the evaluation chamber 1 may be configured without providing the air supply holes 10, that is, configured only by the outer wall 8 by eliminating the inner wall 7 and the air flow passage 9.

Second Embodiment

Figure 9:
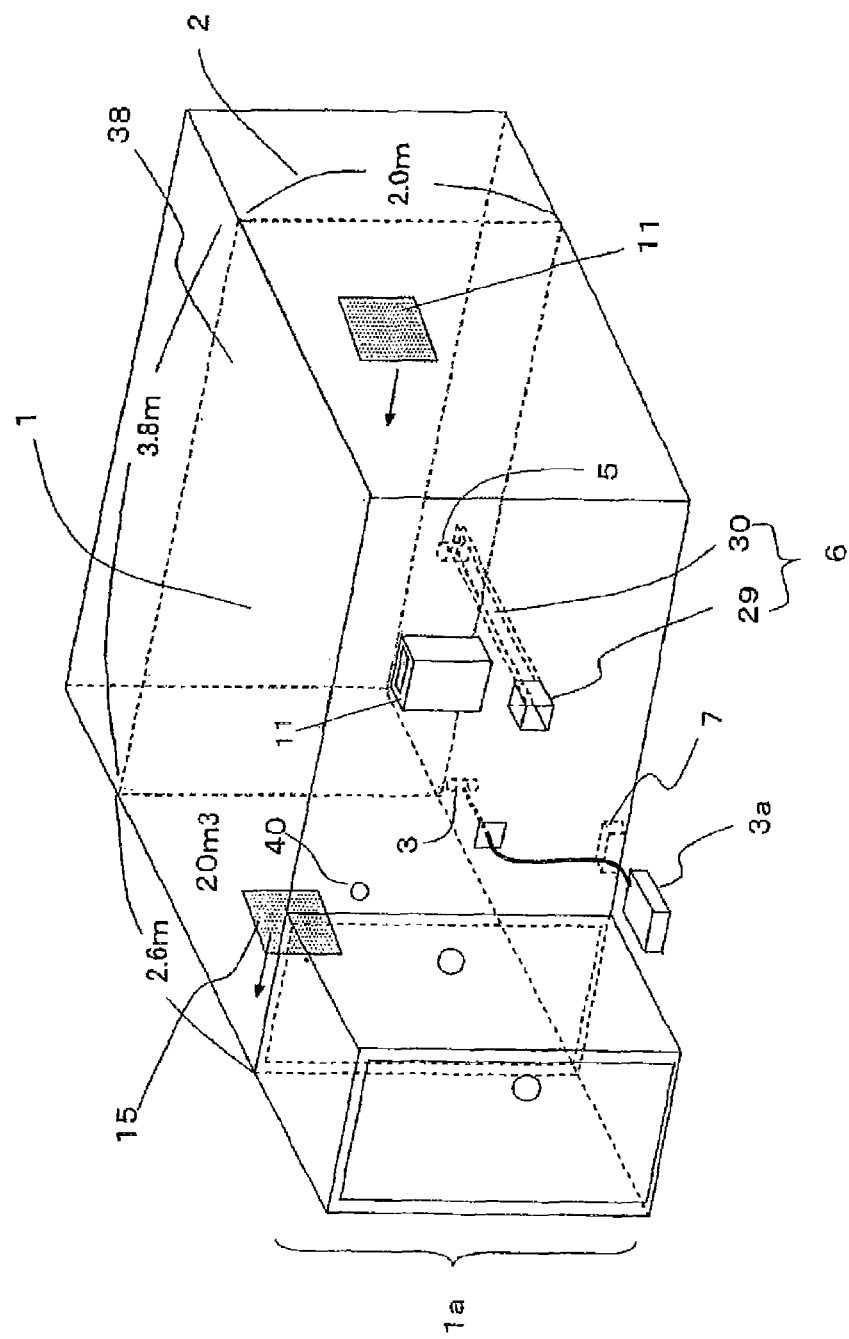
FIG. 9 is a figure showing a schematic configuration of an environmental evaluation installation according to a second embodiment.
Figure 10:
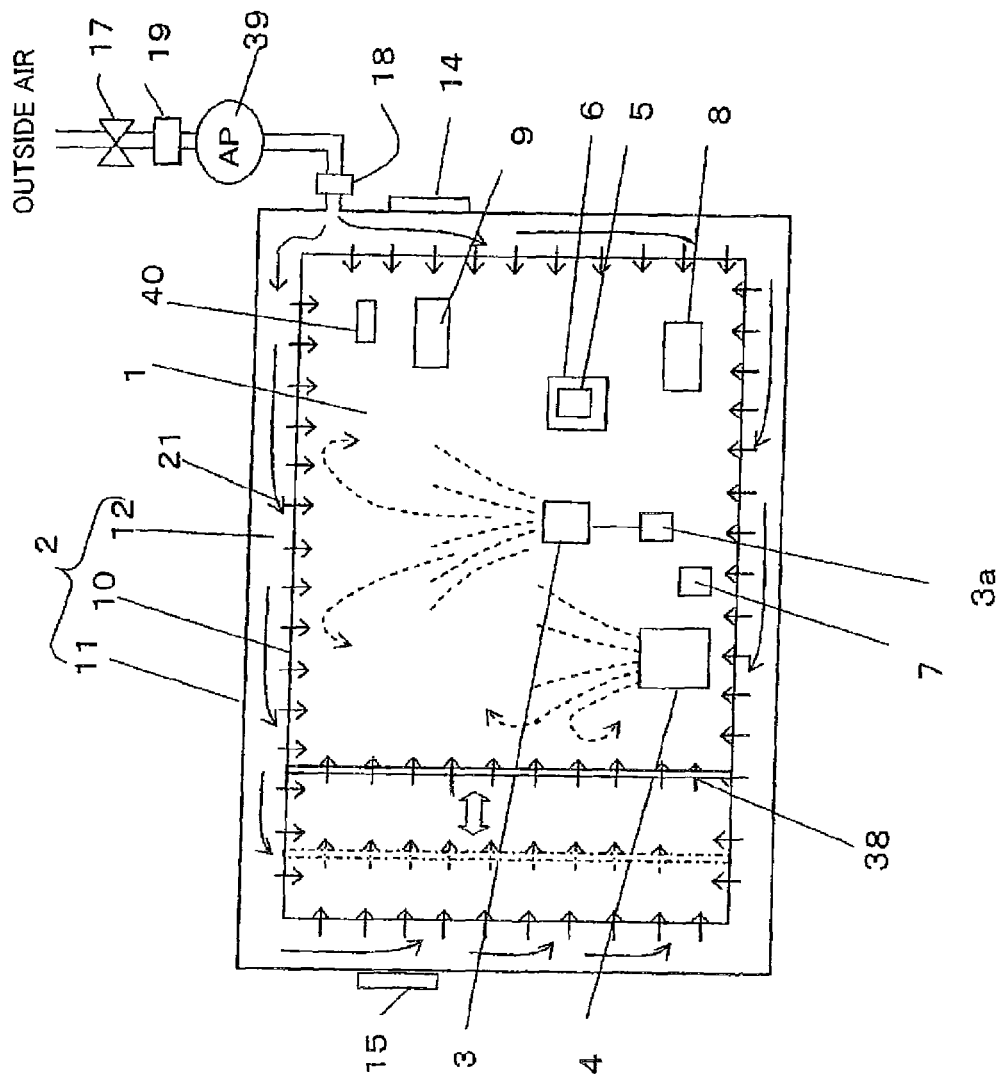
FIG. 10 is a figure showing air flows in the environmental evaluation installation according to the second embodiment.

FIG. 9 is a figure showing a schematic configuration of an environmental evaluation installation according to a second embodiment. FIG. 10 is a figure showing air flows in the environmental evaluation installation according to the second embodiment. As shown in FIG. 9 and FIG. 10, the present embodiment is characterized in that there are provided a movable wall 38 which partitions the inside of the evaluation chamber 1 and which can be moved in the inside of the evaluation chamber 1, and a pump apparatus 39 which sends the air into the air supply pipe 16. The other fundamental configuration of the present embodiment is the same as the configuration of the above described first embodiment, except that the air exhaust opening 22, the exhaust pipe 23, the valve 24, the exhaust amount measuring section 25, the pump apparatus 26, and the impinger 27 are omitted.

The movable wall 38 is moved to be separated from or approach at least one of the walls of the evaluation chamber 1 in the direction vertical to the wall surface. The movable wall 38 can be moved along rails (not shown) provided on the inner surfaces of the isolation walls 2. It is possible to change the volume of the evaluation chamber by moving the movable wall 38. The movable wall 38 is moved in the separating direction automatically in association with the increase in the amount of air introduced from the air supply holes 21 or the increase in the pressure in the evaluation chamber 1 which pressure is measured by the barometer 40.

With the above described configuration, it is possible to prevent the pressure in the evaluation chamber 1 from being increased even when the air is introduced from the air supply holes 21.

Thereby, it is possible to perform the test in which the monitoring time is significantly increased. Also, it is possible to perform an effective and highly reliable test of bacteria or particles for which a significant difference is hard to be confirmed by comparison with the contrast test in a short time.

Third Embodiment

Figure 11:
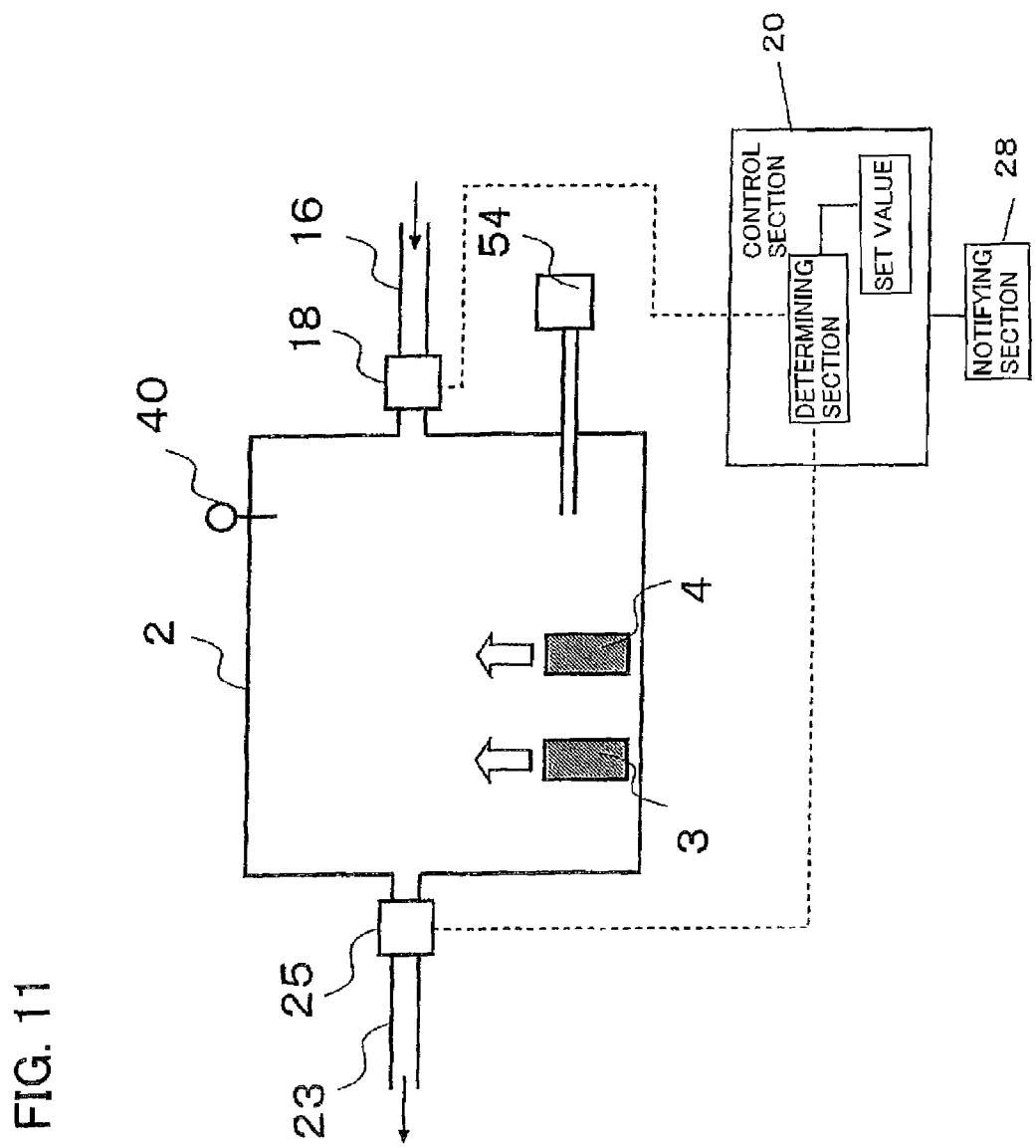
FIG. 11 is a figure showing a schematic configuration of an environmental evaluation installation according to a third embodiment.

FIG. 11 is a figure showing a schematic configuration of an environmental evaluation installation according to a third embodiment. As shown in FIG. 11, the present embodiment is characterized in that the inner wall 10 and the air flow passage 12 are omitted, and that the isolation wall 2 is configured only by the outer wall 11, that is, the air supply holes 21 are omitted. The other fundamental configuration of the present embodiment is the same as the configuration of the above described first embodiment.

Similarly to the first embodiment, the exhaust amount is detected by the exhaust amount measuring section 25, and the detected exhaust amount is notified to the control section 20. On the basis of the detected exhaust amount, the control section 20 controls the pump apparatus so that the exhaust amount is fixed.

Further, the control section 20 determines whether or not the air flow in the evaluation chamber 1 is normal, on the basis of the difference between the exhaust amount from the exhaust amount measuring section 25 and the inflow amount from the inflow amount measuring section 18. For example, when the exhaust amount is smaller than the inflow amount, and when the difference between the exhaust amount and the inflow amount is larger than a predetermined value, it is estimated that the leakage of air from the evaluation chamber 1 is caused. In such a case, a warning is issued by the notifying section 28. As for the form of the notifying section 28, there are listed a display in a display section, such as a monitor, and notification by sound or light.

In this way, in the present embodiment, the inside of the evaluation chamber 1 can be maintained at a weak negative pressure, and hence it is possible to prevent the floating bacteria from being leaked to the outside.

Fourth Embodiment

Figure 12:
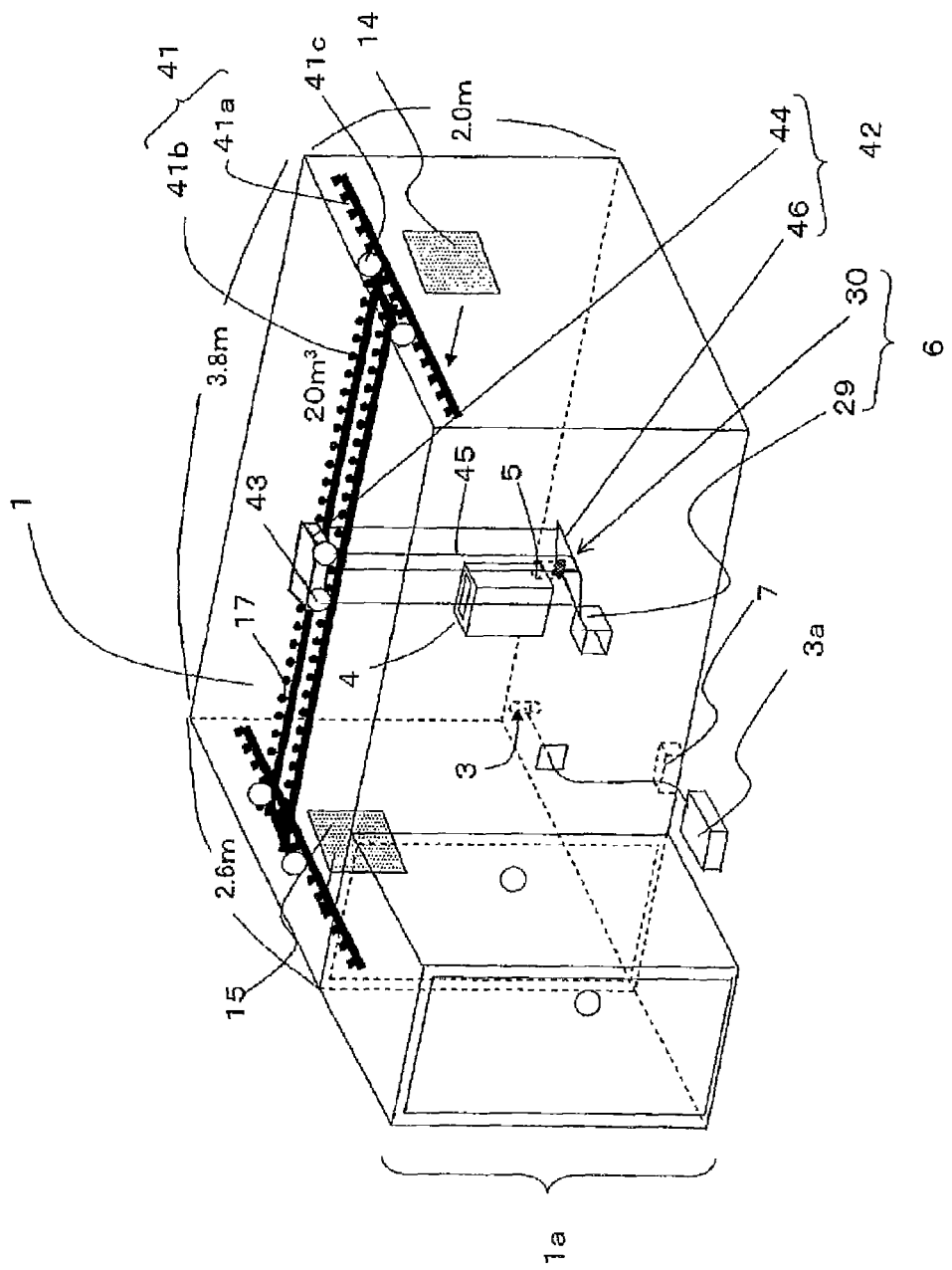
FIG. 12 is a figure showing a schematic configuration of an environmental evaluation installation according to a fourth embodiment.
Figure 13:
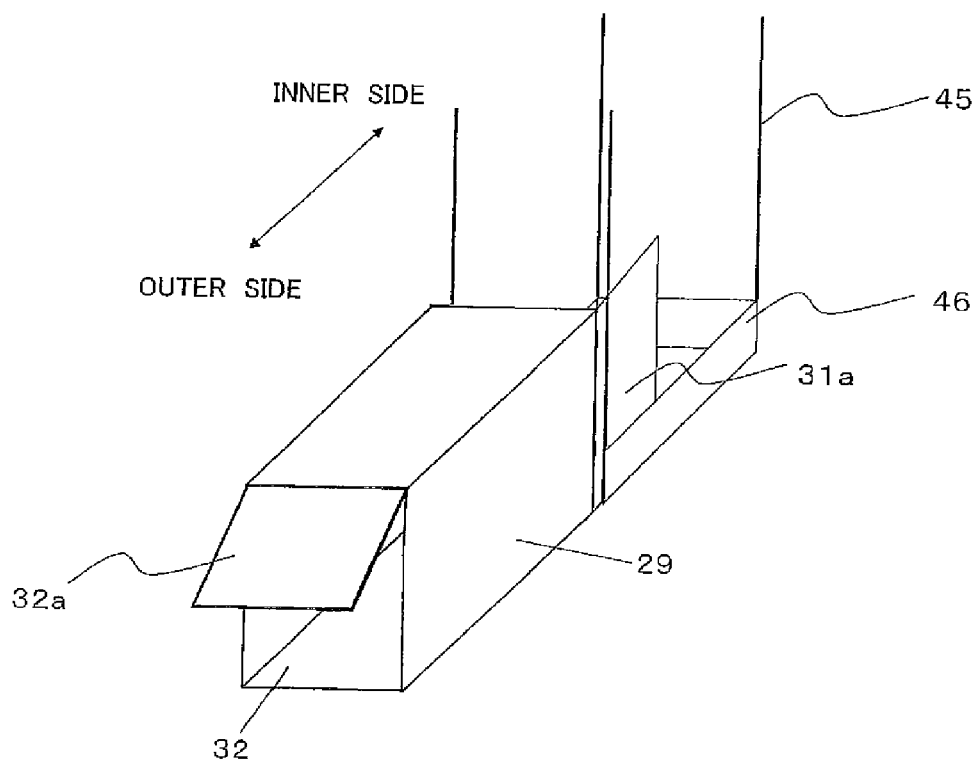
FIG. 13 is a figure showing a configuration of a taking in and out mechanism 6 of the air sampler 5 of the environmental evaluation installation according to the fourth embodiment.

FIG. 12 is a figure showing a schematic configuration of an environmental evaluation installation according to a fourth embodiment. FIG. 13 is a figure showing a configuration of a taking in and out mechanism 6 of the air sampler 5 in the environmental evaluation installation according to the fourth embodiment. As shown in FIG. 12 and FIG. 13, the taking in and out mechanism 6 according to the present embodiment is the same as that of the first embodiment in that the rectangular parallelepiped shaped pass box 29 is provided. However, the taking in and out mechanism 6 according to the present embodiment is different from that of the first embodiment in that the moving means 30 is configured by rails 41 which are installed on the ceiling surface of the evaluation chamber and which serve as the guide passage, and is configured by a movable body 42 which is movable along the rails 41 and which is hung from the ceiling surface. Note that the other fundamental configuration of the present embodiment is the same as the configuration of the above described first embodiment.

The rails 41 are configured by first rails 41a which are provided in parallel with both the side wall surfaces of the evaluation chamber 1, and second rails 41b stretched between the first rails 41a. The second rails 41b have wheels 41c, so as to be made movable on the first rails 41a. The movement of the first rails 41b is remotely controlled.

The movable body 42 is mounted on the second rails 41b. The movable body 42 is configured by a truck 44 which has wheels 43 and which is movable along the second rails 41b, and a mounting board 46 which is hung from the truck 44 by supporting bodies 45 and on which the air sampler 5 is mounted. With this constitution, the movable body 42 can be moved along the second rails 41b.

Further, the truck 44 has a driving section (not shown) for driving the wheels 43, and a receiving section (not shown) configured to be able to be remotely operated, so that the drive of the wheels 43 is remotely controlled. It is possible to freely move the truck 4 along the second rails 41b by the remote operation.

With the above described configuration, the movable body 42 is made movable along the second rails 41b in the right and left direction, and further the second rails 41b themselves are movable forward and backward along the first rails 41*a*. Thereby, as a whole, the movable body 42 can be moved forward, backward, and leftward, rightward in the evaluation chamber 1.

Further, the supporting body 45 is freely wound by pulleys (not shown) provided in the truck 44, and hence it is possible to adjust the height of the mounting board 46 by adjusting the winding degree of the supporting body 45.

Next, there will be described the method for taking the air sampler 5 in and out of the evaluation chamber 1. The mounting board 46 of the movable body 42 is moved to the front of the door 31*a* of the pass box 29 on the side of the evaluation chamber. At this time, the height of the bottom surface of the pass box 29 and the height of the mounting board 46 of the movable body 42 are aligned. Next, the door 32*a* on the side of the outer space and the door 31*a* on the side of the evaluation chamber are opened, and the air sampler 5 provided with the agar medium is directly mounted on the mounting board 46. Immediately, the door 32*a* on the side of the outer space and the door 31*a* on the side of the evaluation chamber are closed. Then, the movable body 42 on which the air sampler 5 is mounted is moved to a predetermined position by combining the movement on the first rail 41*a* and the movement on the second rail 41*b*.

Next, the air sampler 5 is operated by a timer function or a remote control operation, to collect the floating bacteria in the evaluation chamber 1. Note that it is preferred that the collection of the floating bacteria is performed a plurality of times to measure the time-sequential change in the concentration of the floating bacteria.

Further, in order to take out the air sampler 5, the mounting board 46 of the movable body 42 is moved to the front of the door 31*a* of the pass box 29 on the side of the evaluation chamber. At this time, the height of the bottom surface of the pass box 29 and the height of the mounting board 46 of the movable body 42 are aligned. Next, when the door 32*a* on the side of the outer space and the door 31*a* on the side of the evaluation chamber are opened, the air sampler 5 in which the floating bacteria are collected can be taken out.

In the present embodiment, since the position of the air sampler 5 can be moved in the up, down, left and right directions, it is possible to also measure the concentration distribution of the microorganism in the space of the evaluation chamber 1.

INDUSTRIAL APPLICABILITY

The present invention can be effectively used for an environmental evaluation installation and an environmental evaluation method for performing evaluation of minute substances in the space.

The invention claimed is:

1. An environmental evaluation method, comprising:

supplying a plurality of microorganisms into an evaluation chamber isolated by isolation walls from an outer space such that the microorganisms are suspended in air within the evaluation chamber;

supplying removal particles into the evaluation chamber for removing the microorganism from the evaluation chamber, wherein a charged particle, a radical or a particle having a sterilizing ability is used as the removal particles;

collecting a sample of the microorganisms from the evaluation chamber;

measuring the collected sample of the microorganism; and evaluating an ability of the removal particles to remove the microorganism from the evaluation chamber, based on the measurement of the collected sample, wherein for preventing the microorganisms from adhering to the isolation walls, each isolation wall has an outer wall and an inner wall, and via an air flow passage formed between the inner wall and the outer wall, an air current flows, through a plurality of air supply holes formed on all wall surfaces excluding the floor surface of the inner wall or all wall surfaces including the floor surface of the inner wall, into the center of the evaluation chamber while maintaining the inside of the evaluation chamber in the negative pressure state, a plurality of samples are collected and measured periodically during supply of the removal particles into the evaluation chamber, and the ability of the removal particles to remove the microorganism from the evaluation chamber over time is evaluated based on the plurality of measurements, and substantially only spore-forming bacteria in a sporulated state are used as the microorganism in order to prevent the spontaneous decrease of the microorganism from suspension within the evaluation chamber.

2. The environmental evaluation method according to claim 1, wherein the spore-forming bacteria is *Bacillus subtilis*.

3. The environmental evaluation method according to claim 2, wherein measuring the collected sample of the microorganism includes measuring a concentration of the microorganism, a cell infection rate, or an allergic reaction rate.

* * * * *